(12) United States Patent
Hossainy et al.

(10) Patent No.: US 8,753,709 B2
(45) Date of Patent: *Jun. 17, 2014

(54) METHODS OF FORMING COATINGS WITH A CRYSTALLINE OR PARTIALLY CRYSTALLINE DRUG FOR IMPLANTABLE MEDICAL DEVICES

(71) Applicant: Abbott Cardiovascular Systems Inc., Santa Clara, CA (US)

(72) Inventors: Syed Faiyaz Ahmed Hossainy, Hayward, CA (US); Yiwen Tang, San Jose, CA (US); Homayon Askaryar, Newark, CA (US); Qing Lin, Fremont, CA (US); Thierry Glauser, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/722,644

(22) Filed: Dec. 20, 2012

(65) Prior Publication Data

US 2013/0149431 A1 Jun. 13, 2013

Related U.S. Application Data

(63) Continuation of application No. 10/807,546, filed on Mar. 22, 2004, now Pat. No. 8,551,512.

(51) Int. Cl.
*A61L 31/16* (2006.01)
*A61F 2/82* (2013.01)
*A61L 31/10* (2006.01)
*B05D 5/00* (2006.01)

(52) U.S. Cl.
CPC ............. *B05D 5/00* (2013.01); A61L 2300/606 (2013.01); *A61F 2/82* (2013.01); *A61L 31/10* (2013.01); A61L 2300/416 (2013.01); A61L 2420/02 (2013.01); A61L 2300/63 (2013.01); A61L 2420/08 (2013.01); *A61L 31/16* (2013.01)
USPC ...................................................... 427/2.25

(58) Field of Classification Search
None
See application file for complete search history.

(56) References Cited

U.S. PATENT DOCUMENTS

| | | |
|---|---|---|
| 4,540,602 A | 9/1985 | Motoyama et al. |
| 5,637,113 A | 6/1997 | Tataglia et al. |
| 6,153,252 A | 11/2000 | Hossainy et al. |
| 6,207,218 B1 | 3/2001 | Layrolle et al. |
| 6,369,039 B1 | 4/2002 | Palasis et al. |
| 6,579,533 B1 | 6/2003 | Törmälä et al. |
| 6,589,968 B2 | 7/2003 | Arslanian et al. |
| 6,656,216 B1 | 12/2003 | Hossainy et al. |
| 6,926,919 B1 | 8/2005 | Hossainy et al. |
| 7,311,980 B1 | 12/2007 | Hossainy et al. |
| 2002/0032213 A1 | 3/2002 | Navarro et al. |
| 2002/0051845 A1 | 5/2002 | Mehta et al. |
| 2002/0156022 A1 | 10/2002 | Edwards et al. |
| 2002/0165601 A1 | 11/2002 | Clerc |
| 2003/0028244 A1 | 2/2003 | Bates et al. |
| 2003/0051659 A1 | 3/2003 | Rauls et al. |
| 2003/0170287 A1 | 9/2003 | Prescott |
| 2003/0222018 A1 | 12/2003 | Yonker et al. |
| 2005/0004158 A1 | 1/2005 | Iyer et al. |
| 2006/0040971 A1 | 2/2006 | Zhu et al. |
| 2006/0178392 A1 | 8/2006 | Deshmukh |
| 2008/0085880 A1 | 4/2008 | Viswanath et al. |

FOREIGN PATENT DOCUMENTS

| | | |
|---|---|---|
| EP | 1247537 | 9/2002 |
| WO | WO 00/32238 | 6/2000 |

OTHER PUBLICATIONS

Gosselin et al., "Polymorphic properties of micronized carbamazepine procuced by RESS", Int. J. of Pharm. 252, pp. 225-233 (2003).
Kimura et al., "Effects of Aging on Crystallization, Dissolution and Absorption Characteristics of Amorphous Tolbutamide-2-Hydroxypropyl-β-cyclodextrin Complex", Chem. Pharm. Bull. 48(5) 646-650 (2000).
Kolen'ko et al., "On the Possibility of Preparing Fine-Particle Barium Zirconate by Hydrothermal Synthesis", Inorganic Mat. 38(3), pp. 252-255 (2002).
X-Ray Powder Diffraction, downloaded from: www.netlibrary.com/nlreader/nlReader.dll?BookID=12783&FileName=Page_235.html, Dec. 15, 2008, 2 pgs.
Brader et al., *Hybrid Insulin Cocrystals for Controlled Release Delivery*, Nature Biotechnology, vol. 20, pp. 800-804 (2002).
Deschamps, Biomaterials 247 (2) (2004).
Polymorphism in Pharmaceutical Solids, pp. 235-236, Brittain 1999.
Schierholz, *Physico-Chemical Properties of a Rifampicin-Releasing Polydimethylsiloxane Shunt*, Biomaterials 18: pp. 635-641 (1997).
Skarda et al., *Exact and Approximate Solutions to the Double-Diffusive Marangoni-Benard Problem with Cross-Diffusive Terms*, J. Fluid Mech., vol. 366, pp. 109-133 (1998).
Skarda et al., *Exact Solution to Stationary Onset of Convection Due to Surface Tension Variation in a Multicomponent Fluid Layer with Interfacial Deformation*, International Journal of Heat and Mass Transfer 42, pp. 2387-2398 (1999).
Tanny et al., *Effects of Interaction Between Marangoni and Double-Diffusive Instabilities*, J. Fluid Mech., vol. 303, pp. 1-21 (1995).

*Primary Examiner* — Suzanne Ziska
*Assistant Examiner* — Thurman Wheeler
(74) *Attorney, Agent, or Firm* — Squire Sanders (US) LLP

(57) ABSTRACT

Methods for making coatings on an implantable device, such as a drug-eluting stent. The coatings comprise a polymer and a drug in a crystalline or partially crystalline form. In addition, implantable devices produced by the methods and methods of using the coated implantable devices are described.

13 Claims, 1 Drawing Sheet

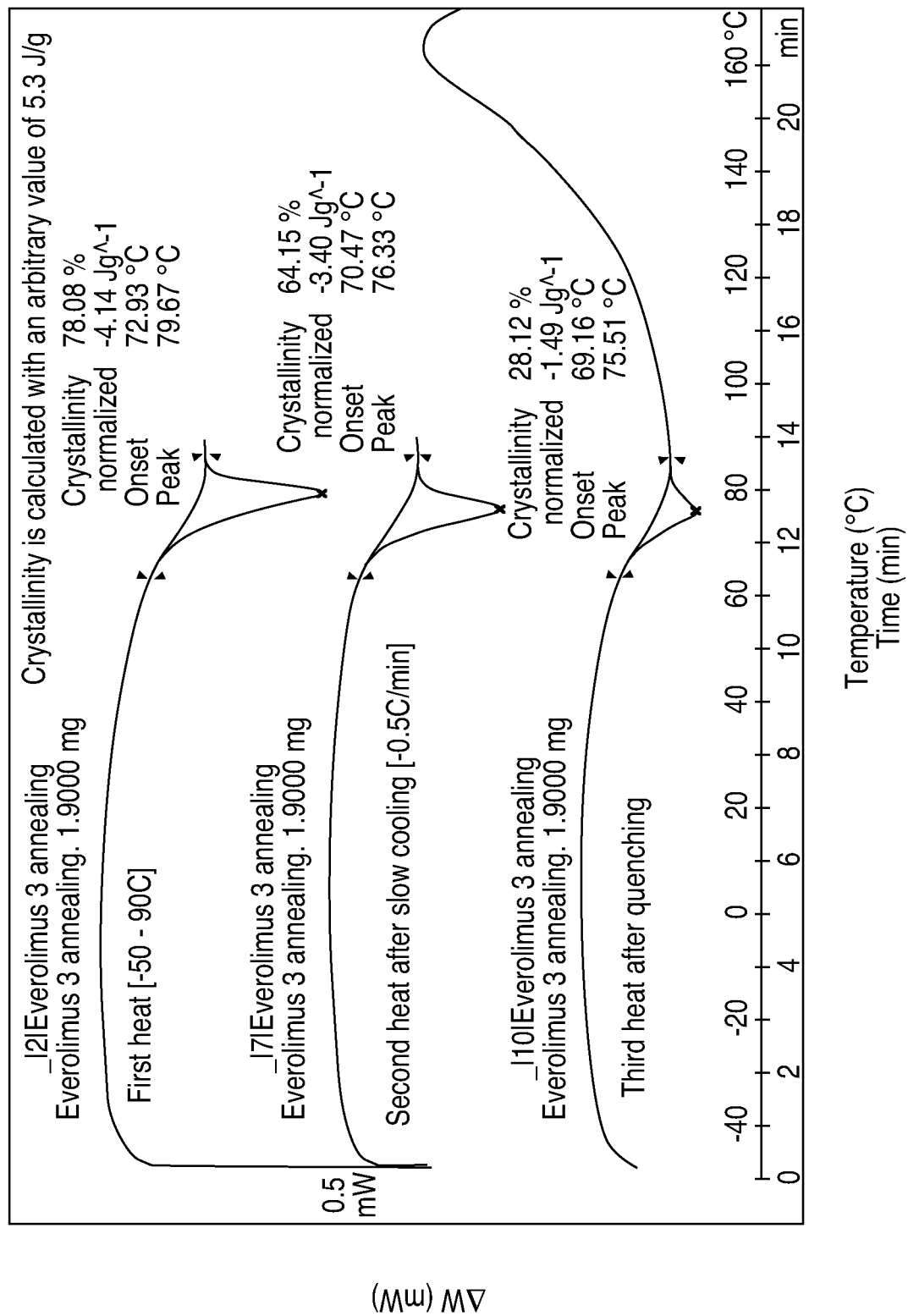

METHODS OF FORMING COATINGS WITH A CRYSTALLINE OR PARTIALLY CRYSTALLINE DRUG FOR IMPLANTABLE MEDICAL DEVICES

CROSS-REFERENCE TO RELATED APPLICATION

This application is a continuation of U.S. application Ser. No. 10/807,546, filed on Mar. 22, 2004, published as United States Patent Application Publication No. 2013-0087270 A1 on Apr. 11, 2013, and issuing as U.S. Pat. No. 8,551,512 B2 on Oct. 8, 2013, which is incorporated by reference in its entirety, including any drawings, herein.

BACKGROUND OF THE INVENTION

1. Field of the Invention

This invention generally relates to drug-eluting coatings comprising one or more drugs in slow-dissolving polymorph having a controlled rate of release.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient. One method of medicating a stent involves the use of a polymeric carrier coated onto the surface of the stent.

Biomaterials with non-fouling characters are in special interest for their good biocompatibility. However, some of these materials provide an inadequate platform for delivery of drugs. Polyethylene glycol/poly(butylene terephthalate) (PEG/PBT) (PolyActive™) is one of the examples. Using PolyActive™ as a top coat for drug-eluting stent has repeatedly shown to reduce platelet deposition in in vitro models. This degradable polymer has shown to have a good mechanical property when coated onto stents. However, previous study indicated that the PolyActive™ could not be used as a matrix polymer because it is incapable of controlling the drug release.

Therefore, there is a need for a material having superior biocompatibility and nonfouling properties that is capable of forming a coating layer on a medical device, such as a stent. Moreover, there is a need for producing a coating made from these materials that provides for adequate release control of a therapeutic substance from the coating.

The embodiments of the present invention address the above described problems and needs.

SUMMARY OF THE INVENTION

Provided herein are methods for making a coating comprising a polymer and a drug in slow-dissolving polymorph for controlled release of the drug. The polymer can be any hydrophilic or hydrophobic polymer. In one embodiment, the polymer can be PolyActive™, poly(ethylene glycol), hyaluronic acid, phosphoryl choline, and combinations thereof. The drug can be any solid drug. In one embodiment, the drug can be any of proteins, peptides, anti-inflammatory agents, antivirals, anticancer drugs, anticoagulant agents, free radical scavengers, paclitaxel, estradiol, steroidal anti-inflammatory agents, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, sirolimus, sirolimus derivatives, 40-O-(2-hydroxy)ethyl-rapamycin (everolimus), 40-O-(3-hydroxy)propyl-rapamycin, 40-[2-(2-hydroxy)ethoxy]ethyl-rapamycin, and 40-O-tetrazole-rapamycin, ABT-578, clobetasol, cytostatic agents, prodrugs thereof, co-drugs thereof, and a combination thereof.

In one aspect of the present invention, the coating comprising nano or microparticles of a drug in slow-dissolving polymorph can be formed by powder spraying the nano or microparticles of a drug in slow-dissolving polymorph on to an implantable device, wrapping the device with a hydrophilic polymer, and heat-treating the hydrophilic polymer to form a coating comprising a hydrophilic polymer and nano or microparticles of a drug in slow-dissolving polymorph.

In another aspect of the present invention, the method described herein comprises inducing the formation of nano or microparticles of a drug in slow-dissolving polymorph in a coating on an implantable device that comprises a polymer and the drug by applying to the implantable device an ultrasound to form in the coating nano or microparticles of the drug in slow-dissolving polymorph.

In a further aspect of the present invention, the method described herein comprises forming a coating comprising a hydrophilic polymer and a drug on an implantable device, and inducing crystallization of the drug by a freeze-thawing process to form a coating comprising nano or microparticles of the drug in slow-dissolving polymorph and the hydrophilic polymer.

In still a further embodiment of the present invention, the method disclosed herein comprises forming a coating comprising a hydrophilic polymer and a drug on an implantable device, and inducing crystallization of the drug by a freeze-drying process to form a coating comprising nano or microparticles of the drug in slow-dissolving polymorph and the hydrophilic polymer.

In still a further embodiment of the present invention, the method disclosed herein comprises forming a coating on an implantable device, and subjecting the coating to supercritical $CO_2$ assisted sorption and subsequent pressure swing to form nano or microparticles of a drug in slow-dissolving polymorph in the coating.

The coatings produced by the methods provided herein have a delayed release profile of the drug. An implantable device comprising the coating can be used to treat a disorder in a human such as stenosis, restenosis, occlusions of the arterial vasculature, vulnerable plaque and combinations thereof.

BRIEF DESCRIPTION OF THE FIGURES

FIG. 1 is a DSC thermogram of everolimus under thermal treatment.

DETAILED DESCRIPTION

Provided herein are methods for making coatings on an implantable device comprising nano or microparticles of one or more drugs in slow-dissolving polymorph. The coating has a controlled release rate of the drug or drugs.

Slow-Dissolving Polymorph

Polymorph refers to the phenomenon of multiple forms of a single compound. Different polymorphs of a single compound have different thermodynamic properties measured by thermodynamic parameters that correspond to stabilities of the polymorphs. A material in different polymorphs has different solubility. Generally, the more thermodynamically stable the polymorph of a compound, the lower the solubility that the compound would have. As used herein, the term "slow-dissolving polymorph" refers to any drug phase other than a slow-dissolving polymorph. A slow-dissolving polymorph of a compound has a relatively higher thermodynamic stability and a relatively smaller solubility. For example, relative to an amorphous state of a compound, the crystalline state of the compound is a slow-dissolving polymorph of the compound.

Thermodynamic factors affect the formation of a particular polymorph. Thermodynamic factors that reduce thermodynamic energy facilitate the formation of slow-dissolving polymorph of a particular drug. Such factors include, but are not limited to, crystallinity, hydrogen bonding and other tertiary interactions. For example, it has been reported that crystallinity of a drug affects the release rate of the drug (Schierholz, et al., Biomaterials, 18:635-641 (1997); Brader, et al., Nature Biotechnology, 20:800-804 (2002)). A higher crystallized pharmaceutical agent will have a slower release rate due to its slower dissolution rate. This has been true for both protein and small molecules (Schierholz 1997; Brader 2002).

Methods for Making Coatings Comprising Crystalline Drug Powders

Powder Spray

In accordance with one aspect of the present invention, a nano or microparticulate drug powder in slow-dissolving polymorph can be coated onto an implantable medical device such as a stent by a powder-spray process. In one embodiment, the process comprises coating a crystalline powder of a drug or drugs onto at least a portion of the surface of an implantable device or a coating layer on the surface of the device by, for example, powder spray or shaking the implantable device in the powder, forming a polymer wrap by wrapping the implantable device on top of the drug powder layer with a polymer, which can be a hydrophilic or hydrophobic polymer film or sheet, and treating the polymer wrap with heating at a temperature sufficient to laminate the wrap. In one embodiment, the temperature is below the melting point of the drug, but above the glass transition temperature of the polymer wrap of the polymer.

The nano or microparticles of the drug or drugs have a size in the range between about 1 nm to about 500 microns, for example, about 1 nm, 10 nm, about 50 nm, 100 nm, 1 micron, 10 microns, about 20 microns, about 50 microns, about 100 microns, about 200 microns, or about 500 microns.

Sonocrystallization

In accordance with a second aspect of the present invention, the coating comprising crystalline drug powder can be generated by sonocrystallization. Sonocrystallization is the use of power ultrasound to control the course of an industrial crystallization process. Ultrasound is used principally to influence the nucleation process, thus giving the engineer or chemist a level of process control and product tailoring previously unobtainable. The use of ultrasound provides a non-invasive way of improving crystal properties and process controllability, chiefly by controlling the size distribution and habit of the crystals. The following benefits of sonocrystallization are: (1) improved product and process consistency, (2) improved crystal purity, (3) improved product secondary physical properties, (4) shorter crystallization cycle times and less frequent rework, and (5) shorter and more reliable downstream processes. In the sonocrystallization process, the power ultrasound used therein creates cavitation in liquid media, each cavitation event comprising the opening of a small (a few tens of microns) gas or vapor void followed by its violent collapse. Cavitation events serve as nuclei for new crystals to form and grow. At high intensities ultrasound can be used instead of seed crystals, and/or to start nucleation at a lesser degree of supersaturation than would normally be the case. By varying the power and duration of insonation the crystal size distribution can be tailored to optimize downstream processing. Insonation to nucleate shows a marked increase in the mean crystal size, whereas continuous insonation has dramatically reduced the mean size.

Generally, an implantable device is first coated with a composition that comprises a drug and a polymeric material. Then sonocrystallization of the drug is performed by applying an ultrasound to the coating to form nano or microparticles of the drug in slow-dissolving polymorph. The nano or microparticles of a drug in slow-dissolving polymorph thus formed can have a crystallinity of about 1%, about 5%, about 10%, about 20%, about 30%, about 40%, about 50%, about 60%, about 70%, about 75%, about 80%, about 90%, about 95%, about 99%, or about 100%.

Induction of Crystallization by Freeze-Thawing

In a third aspect of the present invention, crystallization of the drug can be induced by a freeze-thaw process. In one embodiment, a composition comprising a polymeric matrix or carrier, and one or more drugs is first dissolved in a solvent or solvent mixture. The solution is applied to an implantable device and is then cooled to a temperature below the melting points of the solvent or solvent mixture, the polymeric matrix and the one or more drugs. The temperature is then raised to about the melting point of the solvent. Removal of the solvent allows the formation of a coating comprising nano or microparticles of a drug in slow-dissolving polymorph. The nano or microparticles of a drug in slow-dissolving polymorph thus formed can have a crystallinity of about 1%, about 5%, about 10%, about 20%, about 30%, about 40%, about 50%, about 60%, about 70%, about 75%, about 80%, about 90%, about 95%, about 99%, or about 100%.

Induction of Crystallization and Phase Separation by Freeze-Drying

In a fourth aspect of the present invention, a coating comprising nano or microparticles of a drug in slow-dissolving polymorph can be formed by freeze-drying induced crystallization and phase separation. In one embodiment, a coating composition comprising a polymeric matrix or carrier and one or more drugs are dissolved in a solvent. The solution is applied to an implantable device and subsequently cooled to a temperature below the melting points of the polymeric matrix, the one or more drugs, and the solvent or solvent mixture to form a frozen layer of the solvent or solvent mixture and the coating composition. The implantable device bearing this frozen layer of coating is then subjected to a vacuum at a pressure below the vapor pressure of the frozen solvent or solvent mixture for a period sufficient for removal of the solvent or solvent mixture to form a coating having nano or microparticles of a drug in slow-dissolving polymorph. One exemplary freeze-drying process is lypholizing, in which an implantable device coated with a solution comprising the coating composition is quenched by a low temperature media such as liquid nitrogen and then is removed of the solvent or solvent mixture by vacuum. The nano or microparticles of a drug in slow-dissolving polymorph thus formed can have a crystallinity of about 1%, about 5%, about 10%, about 20%, about 30%, about 40%, about 50%, about 60%, about 70%, about 75%, about 80%, about 90%, about 95%, about 99%, or about 100%.

Induction of Crystallization by Supercritical $CO_2$ Assisted Sorption and Subsequent Pressure Swing In a further aspect of the present invention, a coating comprising a solid drug can be subject to supercritical $CO_2$ treatment to induce crystallization so as to form nano or microparticles in the coating.

The concept of critical pressure is well known to one of ordinary skill in the art. Briefly, the critical pressure or temperature of a fluid is the point on the phase diagram, along the liquid-gas phase boundary, where the phase boundary ends and the liquid and vapor densities become equal to each other. Supercritical is defined as pressure and temperature greater than the critical pressure and temperature of the fluid or above the critical point of the fluid. The table below lists the critical temperature and pressure of three of the useful aforementioned fluids:

| Compound | Critical Temperature ° C. | Critical Pressure psi (atm) |
|---|---|---|
| Carbon Dioxide | 31 | 1077 (73.3) |
| Ethane | 32 | 708 (48.1) |
| Propane | 97 | 624 (42.5) |

Induction of crystallization of the drug in a coating can be achieved by selection of a proper fluid system, which is characterized by surface tension, pressure, temperature, polarity of the fluid, solubility of the drug in the fluid, and solubility and swellability of polymer in the fluid, to induce polymer and drug phase re-organization. Of these factors, surface tension can induce the onset of convection, which is important to drying crystallization of the drug in the coating (Tanny, et al.; J. Fluid Mech., vol. 303:1-21 (1995); Skarda, et al.; J. Fluid Mech., vol. 366:109-133 (1998); Skarda, et al., Int. J. Heat Mass Transfer, vol. 42(13):2387-2398 (1999)). A higher surface tension of the fluid may favor crystallization of the drug. Pressure and temperature of the critical fluid enhances the interaction between the critical fluid and the polymer and drug phase in the coating and thus influence the polymer and drug phase re-organization. A higher pressure and a lower temperature of the fluid may thermodynamically favor crystallization of the drug in the coating. Conversely, a lower pressure and a higher temperature of the fluid may thermodynamically adverse to crystallization of the drug in the coating. Polarity of the supercritical fluid relates to the solubility of the drug and the polymer and the swellability of the polymer and thus would influence the crystallization of the drug in the coating. For example, a non-polar fluid may facilitate the crystallization of a polar drug in the coating. Conversely, a polar solvent may facilitate the crystallization of a non-polar drug in the coating.

The supercritical treatment process can be carried out by any suitable way known in the art. For example, a coated stent can be placed in an apparatus and then exposed to a supercritical fluid for a period of time, for example, about 5 minutes, about 10 minutes, about 20 minutes, about 30 minutes, about 45 minutes, about 1 hr, about 2 hr, or about 5 hr until the drug in the coating attains a crystallinity of about 1%, about 5%, about 10%, about 20%, about 30%, about 40%, about 50%, about 60%, about 70%, about 75%, about 80%, about 90%, about 95%, about 99%, or about 100%. The exposure of the coated stent to the supercritical fluid may be carried out continuously or stopped intermittently. Further, the supercritical fluid treatment process may be carried out under agitation conditions such as stirring and sonication.

In addition to induction of crystallization of the drug in the coating, the supercritical fluid treatment described herein may remove residual solvents or other undesirable ingredients from the coating.

Thermal Treatment

In still a further aspect of the present invention, a coating comprising a solid drug can be subjected to thermal treatment to induce formation of a slow-dissolving phase of the drug. Both the drug phase and the polymer phase can be separately or simultaneously manipulated or thermally treated by temperature-time profile to tailor drug release. In one embodiment, the drug phase and the polymer phase are separately manipulated by temperature-time profile to tailor drug release. In another embodiment, the drug phase and the polymer phase are simultaneously manipulated by temperature-time profile to tailor drug release.

In one embodiment, a drug and polymer coated stent can be heated to the $T_m$ for the drug, followed by a slow and controlled slow cooling down period. The crystallinity of the drug can be increased by maintaining the drug containing polymer coating above the polymer's glass transition temperature, but below the drug' melting point in order to allow diffusion of the drug in through the coating, as well as initiation and growth of drug crystallinities (FIG. 1). FIG. 1 is a DSC thermogram of everolimus, which shows that a higher crystallinity can be achieved by quenching at a slow cooling rate such as a cooling rate of −0.5° C. per minute.

Polymers

The methods provided herein for the preparation of a coating comprising nano or microparticles of a drug in slow-dissolving polymorph can be applied to any coating comprising one or more hydrophilic polymers. In one embodiment, the hydrophilic polymer is a PolyActive™, which is a copolymer comprising a poly(ethylene glycol terephthalate) and poly(butylene terephthalate) (PEGT/PBT) segments (Scheme 1).

Scheme 1

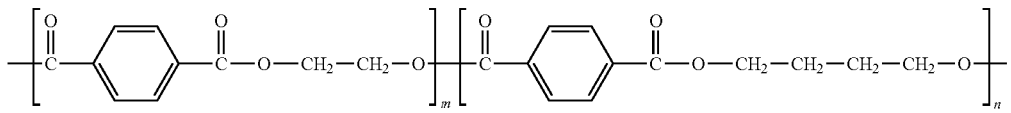

The copolymer can have different ratios of the PEGT segment over the PBT segment. Exemplary PolyActive™ polymers include 4000PEGT80PBT20 and 300PEGT55PBT45, which are commercially available from, for example, IsoTis (Bilthoven, The Netherlands).

In another embodiment, the hydrophilic polymer can be, for example, hyaluronic acid, poly(ethylene glycol), phosphoryl choline based polymers and other hydrophilic polymers having a hydrophilicity comparable to HA, PEG, or phosphoryl choline.

As used herein, the term "hydrophilic polymer" refers to a component having a hydrophilicity comparable or more hydrophilic than PolyActive™, PEG, hyaluronic acid, poly(ethylene glycol), or phosphoryl choline. Generally, hydrophilicity of a polymer can be gauged using the Hildebrand solubility parameter δ. The term "Hildebrand solubility parameter" refers to a parameter indicating the cohesive energy density of a substance. The δ parameter is determined as follows:

$$\delta = (\Delta E/V)^{1/2}$$

where
δ is the solubility parameter, $(cal/cm^3)^{1/2}$;
ΔE is the energy of vaporization, cal/mole; and
V is the molar volume, $cm^3$/mole.
If a blend of a hydrophobic and hydrophilic polymer(s) is used, whichever polymer in the blend has lower δ value compared to the δ value of the other polymer in the blend is designated as a hydrophobic polymer, and the polymer with higher δ value is designated as a hydrophilic polymer. If more than two polymers are used in the blend, then each can be ranked in order of its δ value. For the practice of the present invention, the value of δ of a particular polymer is inconsequential for classifying a polymer as hydrophobic or hydrophilic.

In another embodiment of the present application, the coating described in the present invention may include one or more hydrophobic polymers. Representative hydrophobic polymers include, but are not limited to, ethylene vinyl alcohol copolymer (commonly known by the generic name EVOH or by the trade name EVAL), polyhydroxyalkanoate, poly(hydroxyvalerate), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid) (DLPLA), poly(glycolic acid-co-trimethylene carbonate), polyphosphoester, polyphosphoester urethane, poly(amino acids), cyanoacrylates, poly(trimethylene carbonate), poly(iminocarbonate), polyurethanes, copoly(ether-esters) (e.g. PEO/PLA), polyalkylene oxalates, polyphosphazenes, biomolecules, such as fibrin, fibrinogen, cellulose, starch, collagen and hyaluronic acid, polyurethanes, silicones, polyesters, polyolefins, polyisobutylene and ethylene-alphaolefin copolymers, acrylic polymers and copolymers, vinyl halide polymers and copolymers, poly(amide ester) (PEA), polycaprolactone (PCL), poly(hexafluoro propylene) (HFP), poly(ethylene vinyl alcohol) (EVAL), polyvinyl ethers such as polyvinyl methyl ether, polyvinylidene halides such as polyvinylidene fluoride (PVDF) and polyvinylidene chloride, polyacrylonitrile, polyvinyl ketones, polyvinyl aromatics such as polystyrene, polyvinyl esters such as polyvinyl acetate, copolymers of vinyl monomers with each other and olefins such as ethylene-methyl methacrylate copolymers, acrylonitrile-styrene copolymers, ABS resins, and ethylene-vinyl acetate copolymers, polyamides such as Nylon 66 and polycaprolactam, alkyd resins, polycarbonates, polyoxymethylenes, polyimides, polyethers, epoxy resins, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

In a further embodiment, the coating described herein may include one or more hydrophilic polymer and one or more hydrophobic polymer, both of which are described above.

Bioactive Agents

The polymeric coatings described herein may optionally include one or more bioactive agents. The bioactive agent can be any agent which is biologically active, for example, a therapeutic, prophylactic, or diagnostic agent.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons.

In the case of controlled release, a wide range of different bioactive agents can be incorporated into a controlled release device. These include hydrophobic, hydrophilic, and high molecular weight macromolecules such as proteins. The bioactive compound can be incorporated into polymeric coating in a percent loading of between 0.01% and 70% by weight, more preferably between 5% and 50% by weight.

In one embodiment, the bioactive agent can be for inhibiting the activity of vascular smooth muscle cells. More specifically, the bioactive agent can be aimed at inhibiting abnormal or inappropriate migration and/or proliferation of smooth muscle cells for the inhibition of restenosis. The bioactive agent can also include any substance capable of exerting a therapeutic or prophylactic effect in the practice of the present invention. For example, the bioactive agent can be for enhancing wound healing in a vascular site or improving the structural and elastic properties of the vascular site. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN® available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (bivalirudin, Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, proteins, peptides, anti-inflammatory agents, antivirals, anticancer drugs, anticoagulant agents, free radical scavengers, paclitaxel, estradiol, steroidal anti-inflammatory agents, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, sirolimus, sirolimus derivatives, 40-O-(2-hydroxy)ethyl-rapamycin (everolimus), 40-O-(3-hydroxy)propyl-rapamycin, 40-O-[2-(2-hydroxy)ethoxy] ethyl-rapamycin, and 40-O-tetrazole-rapamycin, ABT-578, clobetasol, cytostatic agents, prodrugs thereof, co-drugs thereof, and a combination thereof.

The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE® and ENDOTAK®, available from Guidant Corporation, Santa Clara, Calif.). The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR® 108, cobalt chrome alloy L-605, "MP35N," "MP20N," ELASTINITE® (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth examples. All parameters and data are not to be construed to unduly limit the scope of the embodiments of the invention.

Example 1

Vision 12 mm small stents were coated with the following configuration:

Primer: a stent was coated with 100 µg PolyActive™ in 2 wt % PolyActive™ (400PEGT80PBT20) solution with mixture of 1,1,2-trichloroethan and chloroform (80/20 by volume), and then baked at 50° C. for 1 hour.

Drug layer: 120 µg pure 40-O-(2-hydroxy)ethyl-rapamycin (everolimus) in 2 wt % drug solution dissolved in acetone/xylene (60/40 by volume); baked at 50° C. for 1 hour.

PolyActive™ layer: 300 µg PolyActive™ in 2 wt % PolyActive™ (300PEGT55PBT45) solution with mixture of 1,1,2-trichloroethan and chloroform (80/20 by volume); baked at 50° C. for 2 hours.

Results

The drug release data for the stent coated with this formulation and configuration indicated a release of 100% at 3 hours in porcine serum.

Example 2

Vision 12 mm small stents were coated according to the following configuration:

Primer: A stent was coated with 200 µg PolyActive™ in 2 wt % PolyActive™ (400PEGT80PBT20) solution with mixture of 1,1,2-trichloroethan and chloroform (80/20 by volume).

After 200 µg polymer coating, the stent was coated another 2 pass of polymer (about 30 µ/pass) and blow dried; the stent was placed into a vial containing 40-O-(2-hydroxy)ethyl-rapamycin (everolimus) powder. By shaking the stent in the powder, about 200 µg drug was coated onto the stent. The stent was coated with two passes of PolyActive™, and followed by drying at 50° C. for 1 hour.

Results

The drug release data for the stent coated with this formulation and configuration showed a release of about 88% of the drug at 24 hours in porcine serum.

Example 3

Vision 12 mm small stent were coated according to the following configuration:

Primer: A stent was coated with 200 µg PolyActive™ in 2 wt % PolyActive™ (300PEGT55PBT45) solution with mixture of 1,1,2-trichloroethan and chloroform (80/20 by volume).

After 200 µg polymer coating, the stent was coated another 2 pass of polymer (about 30 µ/pass) and blow dried; the stent was placed into a vial containing 40-O-(2-hydroxy)ethyl-rapamycin (everolimus) powder. By shaking the stent in the powder, about 200 µg drug was coated onto the stent. The stent was coated with two passes of PolyActive™, and followed by drying at 50° C. for 1 hour.

Example 4

Vision 12 mm small stents were coated with the following configuration:

Primer: a stent was coated with 100 µg PolyActive™ in 2 w t % PolyActive™ (300PEGT55PBT45) solution with mixture of 1,1,2-trichloroethan and chloroform (80/20 by volume), and then baked at 140° C. for 1 hour.

Drug layer: the stent was then coated with 120 µg pure 40-O-(2-hydroxy)ethyl-rapamycin (everolimus) in 2 wt % drug solution dissolved in acetone/xylene (60/40 by volume); baked at 80° C. for 15 minutes, and then slowly cooled down at 0.5° C. per minute using a programmable oven to 50° C. for another 30 minutes.

PolyActive™ layer: the stent was then coated with 300 µg PolyActive™ in 2 wt % PolyActive™ (300PEGT55PBT45) solution with mixture of 1,1,2-trichloroethan and chloroform (80/20 by volume); baked at 50° C. for 2 hr.

Example 5

Vision 12 mm small stents were coated according to the following configuration:

Primer: A stent was coated with 200 µg PolyActive™ in 2 wt % PolyActive™ (300PEGT55PBT45) solution with a mixture of 1,1,2-trichloroethan and chloroform (80/20 by volume) and baked at 140° C. for 1 hr.

Drug/polymer layer: the stent was then 300 µg total solid (everolimus/PolyActive™=2:1) in 2 wt drug-polymer solution with a mixture of 1,1,2-trichloroethan and chloroform (80/20 by volume), without the last dry cycle, put the stent into an 80° C. oven for 15 minute, and then cooled down at 0.5° C. per minute using a programmable oven to 50° C. for another 30 minutes.

Top coat: The stent was then coated with 100 µg PolyActive™ in 2 wt % PolyActive™ (300PEGT55PBT45) solution with a mixture of 1,1,2-trichloroethan and chloroform (80/20 by volume) and baked at 50° C. for 1 hr.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of forming a coating on an implantable medical device, comprising:
   a) applying a powder of a drug in crystalline or partially crystalline form onto at least a portion of an implantable medical device;

b) wrapping the implantable medical device on top of the drug with a sheet of a polymer; and c) heating the sheet of the polymer at a temperature above the glass transition temperature of the polymer to form a coating comprising the polymer on top of the drug.

2. The method of claim 1, wherein the powder of the drug comprises nano- or micro-particles of the drug.

3. The method of claim 1, wherein the polymer is selected from the group consisting of poly(ethylene glycol terephthalate)-co-poly(butylene terephthalate), hyaluronic acid, poly(ethylene glycol), phosphoryl choline, poly(amide ester), poly(D,L-lactide), polyhydroxyalkanoate, polycaprolactone, poly(ethylene vinyl alcohol), and combinations thereof.

4. The method of claim 3, wherein the drug is selected from the group consisting of ABT-578™, paclitaxel, docetaxel, tacrolimus, pimecrolimus, batimastat, mycophenolic acid, estradiol, clobetasol, dexamethasone, rapamycin, everolimus, 40-O-(3-hydroxy)propyl-rapamycin, 40-O-[2-(2-hydroxy)ethoxy]ethyl-rapamycin, 40-O-tetrazole-rapamycin, 4-amino-2,2,6,6-tetramethylpiperidine-1-oxyl (4-amino-TEMPO), and combinations thereof.

5. The method of claim 1, wherein the crystallinity of the drug is selected from the group consisting of about 30%, about 40%, about 50%, about 60%, about 70%, about 75%, about 80%, about 90%, about 95%, about 99%, and about 100%.

6. The method of claim 1, wherein the temperature above the glass transition temperature of the polymer at which the sheet is heated is also below the melting temperature of the drug.

7. The method of claim 1, wherein the drug is everolimus and the polymer is polyethylene glycol terephthalate)-co-poly(butylene terephthalate).

8. The method of claim 6, further comprising maintaining the polymer at the temperature above the glass transition temperature of the polymer and below the melting temperature of the drug such that drug crystallites initiate and grow.

9. The method of claim 6, further comprising maintaining the polymer at the temperature above the glass transition temperature of the polymer and below the melting temperature of the drug to increase the crystallinity of the drug.

10. The method of claim 1, wherein the drug is selected from the group consisting of ABT-578™, paclitaxel, docetaxel, tacrolimus, pimecrolimus, batimastat, mycophenolic acid, estradiol, clobetasol, dexamethasone, rapamycin, everolimus, 40-O-(3-hydroxy)propyl-rapamycin, 40-O-[2-(2-hydroxy)ethoxy]ethyl-rapamycin, 40-O-tetrazole-rapamycin, 4-amino-2,2,6,6-tetramethylpiperidine-1-oxyl (4-amino-TEMPO), and combinations thereof.

11. The method of claim 1, wherein the implantable medical device to which the powder of the drug is applied is coated.

12. The method of claim 11, wherein the implantable medical device is a stent.

13. The method of claim 1, wherein the implantable medical device is a stent.

* * * * *